United States Patent [19]

Sova et al.

[11] Patent Number: 5,143,837

[45] Date of Patent: Sep. 1, 1992

[54] ENZYME COMPLEX HAVING COLLAGENOLYTIC ACTIVITY ISOLATED FROM CRABS

[75] Inventors: Vyacheslav Sova, Petropavlovsk; Alexander Strongyn; Olga Klimova, both of Moscow; Vadim Stadnikov, Petropavlovsk, all of U.S.S.R.

[73] Assignee: Seatec, Moscow, U.S.S.R.

[21] Appl. No.: 534,191

[22] Filed: Jun. 6, 1990

[30] Foreign Application Priority Data

Jun. 9, 1989 [SU] U.S.S.R. .............................. 4700495

[51] Int. Cl.$^5$ .............................................. C12N 9/48
[52] U.S. Cl. ..................................... 435/212; 435/820
[58] Field of Search ................................ 435/212, 820

[56] References Cited

U.S. PATENT DOCUMENTS 3,909,358  9/1975  Stanley et al. ....................... 435/178
4,329,430  5/1982  Klein et al. ........................... 435/212

OTHER PUBLICATIONS

Bavanowski et al, Partial characterization of a . . . J, of Food Science, vol. 49, 1984.
Welgus et al, Degradation of Collagen Substrates, Biochemistry, vol. 22, pp. 2228–2233, 1983.
Grant et al, A Collagenolytic Serine Protease . . . 22, 354–358, 1983.
Grant et al, Substrate Specificity of the Biochemistry, 19, 6089–6095, 1980.
Eisen et al, A Collagenolytic Protease . . . Biochemistry, vol. 12, No. 9, pp. 1814–1822, 1973.
Klimova et al., The Isolation and properties of . . . , BBRC, vol. 166, No. 3, pp. 1411–1420, 1990.
Grant et al., Collagenolytic Protease from Fiddler . . . , Meth. in Enzy., vol. 80, pp. 722–734, 1981.

*Primary Examiner*—David M. Naff
*Assistant Examiner*—Mike Meller
*Attorney, Agent, or Firm*—Kane, Dalsimer, Sullivan, Kurucz, Levy, Eisele and Richard

[57] ABSTRACT

An enzyme complex having collenagenolytic activity, comprising a mixture of collegenolytic proteases from crabs is disclosed. The proteases of the complex have the ability to cleave bovine lens capsule collagen type IV, have molecular weights from about 23,000 to 36,000 daltons, and possess a collagenolytic activity of more than about 3.300 Mandl units/mg at a pH of 7.5. The complex is isolated in aqueous solutions without the use of organic solvents from the hepatopancreas of crabs. The crabs from which the complex can be isolated are of the paralithodes and chinocetes species of crabs.

13 Claims, No Drawings

ENZYME COMPLEX HAVING COLLAGENOLYTIC ACTIVITY ISOLATED FROM CRABS

The invention relates to a collagenolytic activity exhibiting enzyme complex and the method for isolation and purification thereof. Digestase (collagenolytic proteases) will designate hereinafter said complex, able to hydrolyze collagen efficiently.

Due to specific amino acid sequence and spatial structure, different collagen subtypes are significantly resistant to proteolytic attack and cleaved efficiently only by collagenolytic proteases. Collagen is one of the major proteins of connective tissue widely spread in the animal world. Collagen cleavage is necessary for the production of food additives and dermatological preparations, for drugs and creams for cosmestic and medicine, in leather and fur industry, in fish processing industry, in biotechnological industry, in laboratory practice etc. Collagenases are widely used as reagents in molecular biology and immunology for primary cell culture preparation. Conditionally pathogenic microorganisms Clostridium sp. were the traditional source of collagenases, but the level of synthesis of these particular enzymes by microorganisms was rather low, complicating its, large-scale production. Furthermore the microbially-derived enzyme preparations were rather toxic due to the presence of pathogenic and pyrogenic impurities.

Hepatopancreas of deep-water crabs is known to contain collagenolytic proteases (1). Since these particular crabs are scavengers those feed on animal tissues frequently containing collagen, -collagenase substrate-, the presence of a collagenase activity in the hepatopancreas of these animals is not unexpected. These particular deep-water crabs live usually at the depth about 200 meters, the temperature there being about 0 degrees.

The methods for extraction of proteases from crab hepatopancreas using organic solvents are known (2). The known methods are based on the disruption of hepatopancreas tissue in cold acetone at $-20$ degrees C. with a homogenizer, separation of lipids from the pellet fraction containing protease by centrifugation followed by several successive washings of pellet with cold acetone and n-butanol at $-20$ degrees C. The obtained pellet freed from lipids and partially from polysaccharide and protein impurities is dried in vacuo at $-20$ degrees C. above aluminium oxide. The specific activity of protease purified by the described method is not more than hundreds of Mandl units per mg of protein using collagen as a substrate (4). According to (2) protease is further purified with several chromatographic steps including gel-filtration, ion-exchanging and hydroxyapatite chromatography. These methods have several demerits, the main ones being the necessity to use large volumes of organic solvents at the initial stages of protease purification, the necessity to perform the extraction procedure at low temperature ($-20$ degrees C.) and comparatively, low yield and specific activity of the obtained protease. Moreover the described method seems to be unacceptable for the large-scale purification of the enzyme due to the necessity to use fire- and explosion-protected equipment and special protection for staff personnel.

The aim of the invention is the preparation of an enzyme or an enzymatic composition that has good collagenolytic activity and that has not the above demerits or shortcomings.

This is performed by a digestase — a protease complex extracted from hepatopancreas of crabs using only aqueous solvents.

The present invention discloses a digestase from marketable crabs having high collagenolytic activity and a simple and convenient method for the purification of digestase from crab hepatopancreas. More precise description is the following:

Hepatopancreas freezed at $-20$ degrees C. is disrupted with a homogenizer in order to obtain homogeneous suspension, in an appropriate cold (around 4° C.) saline water buffer solution, pH 6.0–9.5, containing 0.1–0.5% nontoxic nonionic detergent and 0.1–2 M of one or several convenient salt(s), such as a metal chloride, to adjust ionic strength. Sodium chloride may be used, but also sea-water, which is unexpensive. This is followed by centrifugation of the prepared homogenate at the same temperature at 3.000–5.000 rpm for 15–30 min. The upper floating lipid layer and pellet are discarded and the supernatant fractions containing digestase are collected and used for the further purification with microfiltration using membrane filters or membrane cassettes with 0.45 micron pore size. The solution passing through the membrane filters is collected. The retentate is resuspended in and washed by 0.1–0.2 M metal chloride water solution under the same conditions of microfiltration to increase the yield of the enzymes of interest. The solutions passing through the membrane filters at the first and the second stages of microfiltration are combined and further purified with ultrafiltration-dialysis through the membrane filters or hollow-fiber filters with cutoff 5 kDa in order to remove low molecular weight impurities, pigments and salts. The final purified, concentrated and dialyzed digestase solution is freeze-dried or spray-dried and stored at 0–4 degrees C.

According to a first aspect of the present invention marketable crabs are the most available source of hepatopancreas, which has been never salvaged before, being up to now the waste of crab catch. Hepatopancreas weight of these crabs mounts to 200 grams, the proteases content being equalled to up 0.5–1% of weight of wet hepatopancreas.

According to a second aspect, the whole extraction process does not use expensive or dangerous organic solvents, but only aqueous saline solutions, or seawater: the raw-material cost is negligible if the plant is installed at sea-side, near a crab-meat factory.

According to a further aspect, the process uses a particular sequence of extraction and purification steps, wherein each individual step can be performed with materials approved at laboratory and plant scale.

According to a still further aspect, digestase samples exhibited, surprisingly, a much higher collagenolytic activity (15.000–20.000 Mandl units/mg towards calf-skin collagen type III) than samples of pure commercial collagenase. For for example, this is 4–5 times higher than the collagenase activity of Clostridium derived purified collagenase (purchased from Serva). Furthermore, all (9–11) digestase fractions separated by FPLC exhibit collagenase activity, depending upon the collagen type.

In contrast with microbial collagenase the crab enzyme complex is able to cleave standard synthetic and protein substrates and possesses a chymotrypsin, trypsin and elastase-like activity.

Digestase is rather stable during storage in water buffers and shows the maximal activity against calf skin collagen Type III as a substrate at pH 7,5. When digestase was kept at room temperature for 4 h at pH 4.0, 7.5 and 9.9 and, then after an appropriate dilution the activity was measured under the standard conditions at pH 7,5, the samples represented 60%, 100% and 80% of the initial activity, respectively. Digestase reveals the highest activity against insoluble collagen Type III at 42° C. and possesses rather low activity at temperature higher than 45° C. 2-5 mM Ca 2+ stabilizes the crab enzymes significantly.

The present invention is further illustrated by the following examples:

EXAMPLE 1

20 kg of Paralithodes camtshatica hepatopancreas freezed at −20 degrees C. c is placed into 40 l aqueous solution of 0,05 M Tris buffer, pH 7.5, containing 0.5% Triton × 100, a nonionic nontoxic detergent, and 1 M Na Cl, and disrupted, to obtain homogeneous suspension, by portions at 4 degrees C. for 30 seconds using a homogenizer-blender at 8.000 rpm. The prepared (ca 60 l) homogenate was centrifuged for 20 minutes at 3.200 rpm. the pellet and upper floating lipid layer were discarded. The supernatant solution of ca 50 l, containing digestase was microfiltrated through membrane filters with the pore size 0.45 micron, using as appropriate equipment "Prostak" (a trade mark of Millipor, France) for 2 h with input and output pressure 1 and 0.4 atm respectively and flux speed 580 ml/min. The concentrated dense suspension (volume ca 15 l) was additionally washed at the same conditions with ca 80 l of 1 M water solution of sodium chloride keeping the volume constant at ca 15 l; the washing was finished when the passing of protein through the membranes became negligible. Protein content in the wash-through solution was measured with the standard methods of protein detection, eg UV-spectrometry. Digestase solutions (ca 100 l) passing through the membranes at the first and the second stages of microfiltration were combined together and concentrated ca three-fold, using an appropriate ultrafiltration equipment (eg. "Pellicon", Millipor, France, or "Romicon", Amicon, Holland) with the 5 kDa cut-off membrane filters or cassettes at the input and output pressure 1 and 0 atm respectively and flux speed 300-480 ml/min. When the volume of concentrated digestase solution equalled ca 30 l, ca 80 l of 1 M water solution of sodium chloride was added and the concentration-dialysis was followed keeping the volume, ca 30 l, constant until the pigmentation of the wash-through solution became negligible. Then ca 100 l of distilled water were added under the same conditions of ultrafiltration-dialysis to remove salts from digestase solution. Finally the digestase solution was concentrated from ca 30 l volume to the volume of 9 l and freeze-dried for 15 h. Freezed-dried solid preparation (180 g) was collected and stored in a refrigerator at 0-4 degrees C. The specific activity of the purified digestase was 11.000 Mandl units per mg of protein (4), the protein content in the solid being > 90%.

EXAMPLE 2

All stages were carried out identically as in example 1, the exception is the use of 40 kg of Chionoecetes opilio hepatopancreas that was homogenized in 120 l of buffer solution. Finally 375 g of freeze-dried powder was obtained with the specific activity 8.300 Mandl unit per mg of protein (4), the protein content in the solid being > 90%.

EXAMPLE 3

All stages were carried out identically as in example 1, the exception is the usage of 0.05 M appropriate Tris buffer at pH 6,0 containing 0.5% of Triton ×100, nonionic nontoxic detergent and 1 M corresponding sodium chloride for isolation. The specific activity of the purified digestase was 7.300 Mandl units per mg of protein (4).

EXAMPLE 4

All stages were carried out identically as in example 1, the exception is the use of 0,05 M appropriate buffer, at pH 9.5, containing 0.5% of detergent and 1 M chloride, for isolation. The specific activity of the purified digestase was 6.200 Mandl units per mg of protein (4).

EXAMPLE 5

All stages were carried out identically as in example 1 the exception is the use of 0.05 M buffer at pH 7.2, containing 0.1% of nonionic nontoxic detergent and 1 M chloride for isolation. The specific activity of the purified digestase was 3.300 Mandl units per mg of protein (4).

EXAMPLE 6

All stages were carried out identically as in example 1, the exception is the desalting and the pigment removal were not carried out. After ultrafiltration concentrated solution undergoes chromatography either on "Biogel G-50" (Trademark of Pharmacia, Sweden) or on analogue of the mentioned carrier with wider range of pores, or on ionexchanging carrier. The specific activity of the purified digestase was within the limits of 10.000-25.000 Mandl units per mg of protein.

EXAMPLE 7

The purification of the individual collagenolytic proteases from digestase was obtained by sephadex G-75 column chromatography (100×2,6 cm) in 50 mM Tris-HCL buffer, pH 7.5, containing 0,1 M Nacl and 1 mM $CaCl_2$, followed by FPLC of the pooled active fractions on a Mono Q column (Pharmacia, 5×50 mm), equilibrated in 10 mM Tris-HCL buffer, pH 8,8 containing 1 mM $CaCl_2$. The individual proteases were eluted. in general, 9-11 protease fractions can be separated with the linear gradient from 0 to 0.5 M NaCl in the same buffer.

Apparent molecular weights, ranking from 23-36 K Da were estimated with SDS - PAGE technique; the electrophoresis was performed in 12.5% polyacrylamide gel in the presence of SDS. The individual proteases isolated from digestase differ from each other by the ability to cleave different protein substrates. As example, illustrated in table 1, "28 kDa"- protease has. lower activity with fibrillar collagen Type 1 from rat skin as compared with that of "36 dKa-C" protease. The most striking feature of the individual crab proteases and digestase is the ability to cleave bovine lens capsule collagen Type IV, which is resistant to Clostridium enzymes. Individual proteases have also specific activities against synthetic small peptides for example N-benzoyl-L-arginine ethyl ester or N-benzoyl-L-tyrosine ethyl ester.

TABLE 1

The specific activity of the enzymes against protein substrates, expressed in arbitrary units/mg of enzyme

| Enzyme | Specific activity against | | | |
| --- | --- | --- | --- | --- |
| | Collagen Type I | Collagen Type IV | Casein | Hemoglobin |
| Digestase | 660 | 516 | 63600 | 1800 |
| "28 kDa"-protease | 264 | 384 | 23280 | 1020 |
| "36 kDa-C"-protease | 386 | 486 | 25920 | 1170 |
| Clostridium histolyticum | | | | |
| collagenase I | 1416 | 0 | 0 | 0 |
| collagenase II | 1854 | 0 | 0 | 0 |

In summary it is clear that crab hepatopancreas contains a powerful mixture of serine proteases with non-identical specificities, that explains the synergism of their action on protein substrates (individual proteases are less active against proteins as compared with digestase).

REFERENCES

1. A. Z. EIZEN Biol Bull. (Woods Hole, Mass) v.133, p.463 (1967).
2. G. A. GRANT, A. Z. EIZEN, R. A. BRADSHOW Methods of Enzymology v. 80, p. 722 (1981)
3. I. MANDL et al. J. CLIN Invest. v. 32, p. 1323 (1953)

We claim:

1. An enzyme complex having collagenolytic activity, comprising a mixture of collagenolytic proteases from crabs, said collagenolytic proteases having the ability to cleave bovine lens capsule collagen type IV and having molecular weights of from about 23,000 to 36,000 daltons wherein said enzyme complex is isolated in aqueous solutions, without the use of organic solvents, from hepatopancreas of crabs, and wherein said crabs are selected from the group consisting of paralithodes and chionocetes species and said enzyme complex possesses a collagenolytic to activity of more than about 3.300 Mandl units/mg at pH 7.5.

2. An enzyme complex according to claim 1, wherein said proteases have non-identical proteolytic and in particular collagenolytic specificities.

3. An enzyme complex according to claim 2, wherein said enzyme complex can be fractionated into at least 9 fractions of the proteolytic complex from crabs hepatopancreas.

4. An enzyme complex according to claim 3, wherein said aqueous solutions comprise 0.1 to 2 M salts, buffers for buffering said solution between pH = 6 and pH = 9.5, and 0.1–0.5% of a nonionic nontoxic detergent.

5. An enzyme complex according to claim 4, wherein said aqueous solution comprises sea-water.

6. An enzyme complex according to claim 5, wherein said hepatopancreas is obtained from crabs selected from the group consisting of paralithodes camtshatica of chionocetes opilio.

7. An enzyme complex as set forth in claim 1 wherein said enzyme complex is isolated in aqueous solutions using membrane separation techniques.

8. An enzyme complex according to claim 7, wherein said membrane separation technics comprise microfiltration and ultrafiltration.

9. An enzyme complex according to claim 8, wherein said microfiltration and said ultrafiltration are carried out using devices selected from hollow-fiber, membrane-filter, membrane-cassette and tangential-flow devices.

10. An enzyme complex according to claim 8, wherein said ultrafiltration is followed by gel-chromatography.

11. An enzyme complex according to claim 7, wherein said hepatopancreas is suspended in an aqueous suspension solution comprising buffers, salts and nonionic nontoxic detergent, submitted to centrifugation for separating an aqueous supernatant from pellets and lipid layers, wherein said supernatant is submitted to microfiltration at a pore size of 0.45 $\mu M$ to obtain a microfiltrated solution, wherein said microfiltrated solution is submitted to ultrafiltration through filters having a cut off at 5 kDa to obtain a concentrated solution.

12. An enzyme complex according to claim 1, wherein said concentrated solution is submitted to gel-chromatography.

13. An enzyme complex according to claim 11, wherein said concentrated solution is dialysed and dried by a technic selected from freeze-drying and spray-drying.

* * * * *